(12) United States Patent
Udale

(10) Patent No.: US 9,429,560 B2
(45) Date of Patent: Aug. 30, 2016

(54) CELL GRABBER WITH UNITARY CONSTRUCTION

(71) Applicant: IonOptix LLC, Milton, MA (US)

(72) Inventor: Richard T. Udale, Roslindale, MA (US)

(73) Assignee: IONOPTIX LLC, Westwood, MA (US)

( * ) Notice: Subject to any disclaimer, the term of this patent is extended or adjusted under 35 U.S.C. 154(b) by 0 days.

(21) Appl. No.: 14/476,056

(22) Filed: Sep. 3, 2014

(65) Prior Publication Data

US 2015/0071832 A1   Mar. 12, 2015

Related U.S. Application Data

(60) Provisional application No. 61/874,591, filed on Sep. 6, 2013.

(51) Int. Cl.
*G01N 33/483* (2006.01)
*G01N 3/04* (2006.01)
*G01N 15/10* (2006.01)

(52) U.S. Cl.
CPC ............ *G01N 33/4833* (2013.01); *G01N 3/04* (2013.01); *G01N 15/10* (2013.01); *G01N 2015/105* (2013.01); *G01N 2015/1006* (2013.01); *G01N 2203/0276* (2013.01)

(58) Field of Classification Search
CPC .. G01N 33/4833; C12M 25/00; G02B 21/32
See application file for complete search history.

(56) References Cited

U.S. PATENT DOCUMENTS

| | | | | |
|---|---|---|---|---|
| 4,762,405 A * | 8/1988 | Inoue et al. | ................... | 359/371 |
| 5,457,041 A * | 10/1995 | Ginaven | ........... | A61M 37/0015 |
| | | | | 435/285.1 |
| 5,843,644 A * | 12/1998 | Liotta et al. | ................. | 435/6.12 |
| 6,241,739 B1 * | 6/2001 | Waldron | ................ | A61B 17/54 |
| | | | | 606/131 |
| 6,358,749 B1 * | 3/2002 | Orthman | ....................... | 436/177 |
| 6,661,575 B1 * | 12/2003 | Yakovenko | ............ | G02B 21/32 |
| | | | | 359/393 |
| 8,268,264 B2 * | 9/2012 | Lenz | ............................. | 422/527 |
| 2005/0121411 A1 | 6/2005 | Cohen | | |
| 2006/0198764 A1 * | 9/2006 | Zimmermann | ........ | G02B 21/34 |
| | | | | 422/536 |
| 2007/0134784 A1 * | 6/2007 | Halverson et al. | ........ | 435/287.2 |
| 2008/0038812 A1 * | 2/2008 | Elson et al. | ............... | 435/287.1 |
| 2009/0000400 A1 * | 1/2009 | Hayles et al. | ............. | 73/863.12 |
| 2009/0149918 A1 | 6/2009 | Krulevitch et al. | | |
| 2012/0034620 A1 | 2/2012 | Ward et al. | | |
| 2012/0096955 A1 | 4/2012 | Guth et al. | | |

OTHER PUBLICATIONS

Fabiato, A., and F. Fabiato, "Contractions Induced by a Calcium-Triggered Release of Calcium From the Sarcoplasmic Reticulum of Single Skinned Cardiac Cells", The Journal of Physiology, Aug. 1975, 469-495, 249 (3).

(Continued)

*Primary Examiner* — Jill Warden
*Assistant Examiner* — Matthew Krcha
(74) *Attorney, Agent, or Firm* — Michael W. Ferrell

(57) ABSTRACT

A cell grabber has a unitary structure including a transparent grabber head at a terminus thereof and an elongated mounting portion extending therefrom for attachment to a force transducer. The grabber head has a planar or concave bonding surface which is coated with an adhesive film to secure the specimen, especially single cells, for tensile measurements. The cell grabber may be used in connection with auxotonic, isometric or isotonic force measurement systems.

20 Claims, 9 Drawing Sheets

(56) References Cited

OTHER PUBLICATIONS

Iribe, Gentaro, et al. "Force-Length Relations in Isolated Intact Cardiomyocytes Subjected to Dynamic Changes in Mechanical Load", American Journal of Physiology. Heart and Circulatory Physiology, Mar. 2006, H1487-H1497. doi:10.1152/ajpheart.00909.2006.

Tajitsu, Y. "Piezoelectricity of Chiral Polymeric Fiber and Its Application in Biomedical Engineering" IEEE Transactions on Ultrasonics, Ferroelectrics, and Frequency Control, May 2008, 1000-1008, 55 (5). doi 10.1109/TUFFC.2008.746.

Brady, A. J., "Mechanical Properties of Isolated Cardiac Myocytes", Physiological Reviews, Apr. 1991, 413-428, 71 (2).

Prosser, Benjamin L., et al., 2011, "X-ROS Signaling: Rapid Mechano-Chemo Transduction in Heart", Science, Sep. 9, 2011, 1440-1445, 333 (6048), New York, N.Y. doi:10.1126/science.1202768.

SI-H CT Micro-Tweezer, Brochure, undated.

* cited by examiner

DETAIL A

DETAIL C

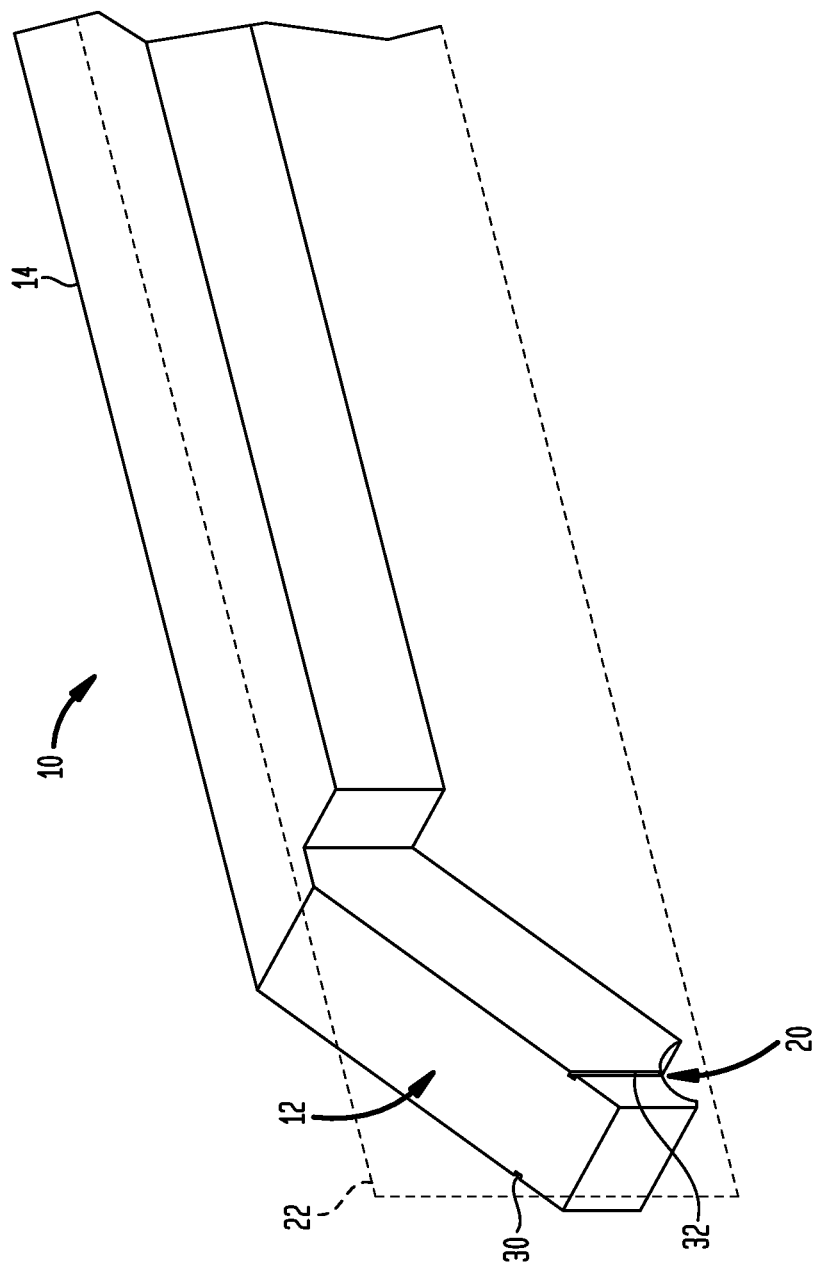

CELL GRABBER WITH UNITARY CONSTRUCTION

CLAIM FOR PRIORITY

This application is based on U.S. Provisional Application No. 61/874,591 of the same title filed on Sep. 6, 2013, the priority of which is hereby claimed and the disclosure of which is incorporated herein by reference.

TECHNICAL FIELD

The present invention relates to a biological specimen holder used together with an adhesive or attachment factor in order to secure the specimen for tensile measurements. In a preferred embodiment, the holder has a concave bonding surface defining a cylindrical section profile which has a radius of curvature in the range of from 20 to 50 microns so as to be suitable to grab a single cell.

BACKGROUND

Accurate measurements of cellular mechanical properties are critical to understand a cell's biological response to its environment. The quality of mechanical measurements depends greatly on the attachment method of the apparatus to the cell specimen. Attachment methods for single-cell specimens are much more tedious than those used on multi-cell specimens. There are no available external attachment locations forcing the apparatus to attach directly to the cell membrane. Therefore, the attachment method must not disturb the specimen while still providing strong enough attachment strength to allow for the application of large forces to the specimen. There have been a number of proposed attachment methods including wrapping, glass micro-needles, and suction micropipettes. Reference is made to the following: Fabiato, A., and F. Fabiato, 1975, "Contractions Induced by a Calcium-Triggered Release of Calcium From the Sarcoplasmic Reticulum of Single Skinned Cardiac Cells . . . ." *The Journal of Physiology* 249 (3) (August): 469-495; Iribe, Gentaro, Michiel Helmes, and Peter Kohl. 2006, "Force-Length Relations in Isolated Intact Cardiomyocytes Subjected to Dynamic Changes in Mechanical Load . . . ." *American Journal of Physiology. Heart and Circulatory Physiology* 292 (3) (March): H1487-97, doi:10.1152/ajpheart.00909.2006; Tajitsu, Y. 2008 "Piezoelectricity of Chiral Polymeric Fiber and Its Application in Biomedical Engineering" *IEEE Transactions on Ultrasonicsm, Ferroelectronics, and Frequency Control* 55 (5) (May): 1000-1008. doi 10.1109/TUFFC.2008.746; Brady, A. J., 1991, "Mechanical Properties of Isolated Cardiac Myocytes . . . . " *Physiological Reviews* 71 (2) (April): 413-428; Prosser, Benjamin L., Christopher W. Ward, and W. J. Lederer, 2011, "X-ROS Signaling: Rapid Mechano-Chemo Transduction in Heart . . . ." *Science (New York, N.Y.)* 333 (6048) (September 9): 1440-1445, doi: 10.1126/science.1202768; Krulevitch et al.; Cohen, A. L., "Medical Devices and EFAB Methods and Apparatus for Producing Them" 2005; Publication No. US2005/0121411; as well as United State Patent Publication US 2012/0096955 of Guth et al. which relates to an S I Instruments Brochure, undated. The cell micrograbber is described in the brochure as a hollow metal tube with two tapered tweezer tips of custom design which in a closed position has a thin, stainless steel rod running through the center of it. When the rod is pushed towards the tip using the control box, the fingers of the tip open to allow the tweezers to grasp a muscle fiber. As the stainless steel rod retracts, the tweezers close and hold the fiber. The device is relatively complex to fabricate and operate and has a limited range of utility in terms of force levels.

As will be appreciated from the foregoing, auxotonic, isometric and isotonic force measurement systems have all been employed to measure cell characteristics in various environments, employing various cell attachment mechanisms and devices of various complexity.

Adhesives have also been used to attach single-cell specimens with various attachment methods and devices described in the foregoing references. Silicon, poly-1-lysine, "Great Stuff" by Dow Chemical, and cyanoacrylate glue are known to have been used. With some of these adhesives preparation time is extended because the adhesives require an extended amount of time to set and some can only be used on skinned myocytes. While cyanoacrylate glue sets quickly and provides a strong grip, exposure will kill the cell in a short period of time, leaving a small window of opportunity to test the specimen. Other adhesives are available that are specifically marketed for cell adhesion. These include ECM gel from Sigma-Aldrich, Inc., Matrigel® and Cell-Tak® from BD Biosciences, Inc. Matrigel® and the ECM gel from Sigma-Aldrich are extra-cellular matrices ("ECMs") derived from Engelbreth-Holm-Swarm mouse sarcoma. Both are too viscous and allow for specimen movement during mechanical testing. Cell-Tak® is a bioadhesive derived from the polyphenolic proteins of marine mussels. More recently, a biocompatible and stronger, more effective and easily processable adhesive was developed and is available through IonOptix (Milton, Mass., Dublin, Ireland). This product is available under the name IonOptix Myotak®. These compositions are described generally in United States Patent Application Publication No. 2012/0034620 of Ward et al.

Despite advances in the art, there exists a pressing need for a more effective cell gripping system which is not destructive or lethal to the cell and allows for measurement of stronger forces applied by or to a live specimen. Simplicity of fabrication and operation are likewise desirable features.

SUMMARY OF INVENTION

There is provided in accordance with the present invention a cell grabber having a unitary structure including a transparent grabber head at a terminus thereof and an elongated mounting portion extending therefrom for attachment to a force transducer. The grabber head is configured and adapted to bond to a live tissue specimen and has a bonding surface which is either planar or concave. In use, the bonding surface is coated with an adhesive film to secure the specimen, especially single cells, for tensile measurements. The inventive device is conveniently fabricated by laser etching a glass cover slip to produce an ensemble of detachable cell grabbers of monolithic construction affixed to a residual carrier member of the substrate from which the ensemble was etched. Other manufacturing techniques such as photolithography may also be employed.

Preferred adhesives for use with the cell grabber are biocompatible adhesives which include an extracellular matrix protein such as laminin, collagen type I, collagen type II, collagen type III, collagen type IV, collagen type V, elastin, entactin, fibronectin, tenascin, heparin sulfate, chondroitan sulfate, dermaten sulfate, karatan sulfate, or combinations of these materials.

Specific embodiments and illustration of construction and operation of the inventive cell grabber as well as further aspects and advantages of the present invention will become apparent from the detailed discussion which follows.

DESCRIPTION OF DRAWINGS

The invention is described in detail below in connection with numerous embodiments and in connection with the attached Figures wherein like numerals and letters designate like parts and features. In the Figures:

FIG. 11A is a view in perspective of another embodiment of a cell grabber of the present invention;

DETAILED DESCRIPTION

Figure 1:
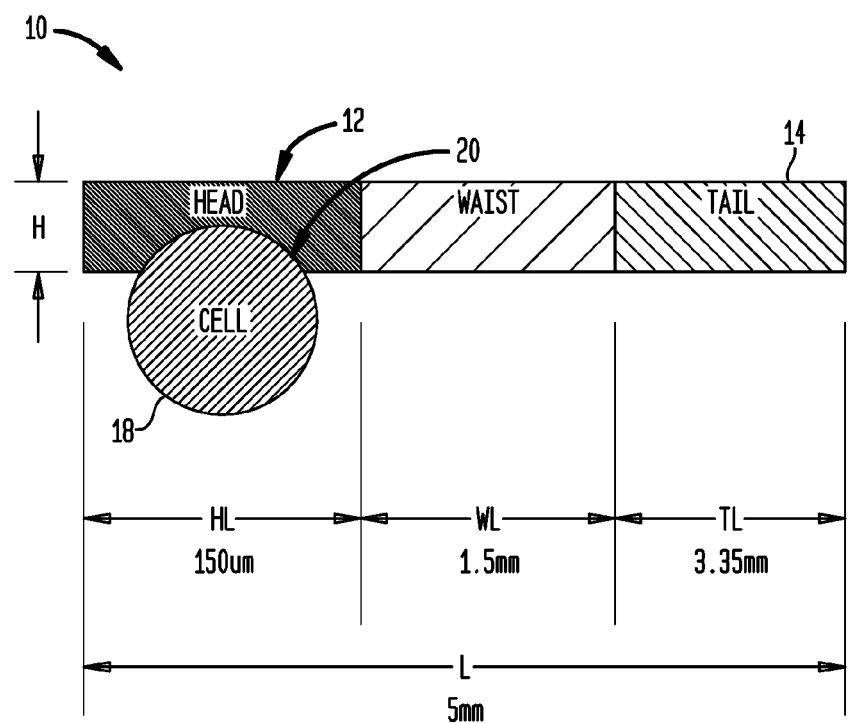
FIG. 1 is a schematic side view in elevation and section of a cell grabber of the invention bonded to a single cell.

The invention is described in detail below in connection with the Figures for purposes of illustration, only. The invention is defined in the appended claims. Terminology used throughout the specification and claims herein are given their ordinary meanings as supplemented by the discussion immediately below.

"Adhesive" refers to attachment factors now used or hereinafter developed which are suitable for adhering a cell or tissue to a substrate for testing. Suitable attachment factors include polylysine/fibronectin coatings, or for example, a collagen based attachment factor. Especially preferred are adhesives of the class MYOTAK® biocompatible adhesives which are described in United States Patent Application Publication No. 2012/0034620 of Ward et al., the disclosure of which is incorporated by reference. Adhesives also include extracellular matrix proteins with or without bond strength agents or aggregates. An adhesive is considered biocompatible if contact with the adhesive for 60 minutes is not lethal to the cell.

As used herein, "aggregate" refers to any composition added to the bio-adhesive composition which results in an increased stability and a larger surface area for attachment. Known aggregates include alumina silicate or diamond powder, and range from approximately 0.1 microns 10 microns or for example from approximately 0.1 micron to 3 microns in diameter depending on the apparatus interface and the type of specimen.

The following terms are used to refer to known types of cell tensile measurements and apparatus therefor: "auxotonic" refers to systems involving contractions which increase in force as the specimen shortens; "isometric" refers to systems where the specimen length is constant and "isotonic" refers to systems where the tension in the specimen remains constant.

"Bond strength agents" refers to components for increasing bond strength and polymerization. These may include for example, collagen type IV, laminin, and/or chitosan. Accordingly, non-limiting example bond strength agents may include at least one component selected from the group consisting of collagen type IV, laminin, and chitosan.

As used herein, "Bovine Serum Albumin" or "BSA" refers to the protein serum itself as well as bovine serum albumin conjugated with a fluorophore. The addition of bovine serum albumin in the adhesive composition allows for fluorophore retention within the composition. The flurophore within the composition allows it to be identified and imaged through microscopy when desired. Imaging may be particularly important to verify that the point of contact on the apparatus is properly coated before attaching the specimen. The composition may be conjugated to a flurophore of choice by adjusting the BSA conjugate in the composition. Other matter having similar fluorophore retention properties are believed to likely be effective as well.

As used herein, "chitosan" refers to a linear polysaccharide composed of randomly distributed β-(1-4)-linked D-glucosamine (deacetylated unit) and N-acetyl-D-glucosamine (acetylated unit). (Harrison K. Chitosan @ 3Dchem.com. 2009. http://www.3dchem.com/molecules.asp?ID=444). Chitosan is produced commercially by deacetylation of chitin which is the structural element in the exoskeleton of many crustaceans. (Harrison K. Chitosan@3Dchem.com. 2009. http://www.3dchem.com/molecules.asp?ID=444).

"Concave" is used in its general geometrical sense, that is, a concave element defines a cavity such that the concave element cavity has a surface area larger than its projected perpendicular area.

As used herein, "extracellular matrix," "extracellular matrix proteins," and "extracellular matrices" refer to a matrix composed of a variety of proteins and polysaccharides the major constituents of which are collagens, non-collagenous glycoproteins, and proteoglycans, such as, for example, laminin, collagen type I, collagen type II, collagen type III, collagen type IV, collagen type V, elastin, entactin, fibronectin, tenascin, heparin sulfate, chondroitan sulfate, dermaten sulfate, or karatan sulfate. (Alberts, Johnson, Lewis, Raff, Roberts, Walter, "The Extracellular Matrix of Animals", Molecular Biology of the Cell, 4th edition. 2002: Chapter 19). By way of non-limiting example, the extracellular matrix may be an extracellular matrix gel. Extracellular matrix protein may be derived from Engelbreth Holm-Swarm sarcoma.

"Monolithic" refers to a structure formed from a single piece of material. The various parts a monolithic structure are considered integral therewith.

"Myocytes" refers to contractile biological cells, such as skeletal and cardiac muscle cells.

"Planar" means a flat structure with preferably with little or no radius of curvature at all; in some embodiments relatively flat surfaces may have convexity or concavity with a radius of curvature of more than 1 mm, if so desired. Surfaces with such curvature are considered substantially flat on a cellular scale.

A "rectangular" monolithic structure has 4 flat sides as is illustrated in the in the various Figures, wherein each portion of the device may have rectangular cross sections of different sizes as described herein. Preferably the sides are orthogonal to adjacent sides, but +/−10 degrees is considered a substantially rectangular structure.

The cell gabber head and preferably the entire articles of the invention are transparent in that they substantially freely transmit visible light without scattering the light to a degree which impairs observation of the specimen. Tinting may be employed if not detrimental to clarity of the grabber head. Typically, the articles will exhibit Haze values of less than 50% and Transmittance values of more than 75% (ASTM Test Method D 1003-00B) at 100 micron thickness. The cell grabbers of the invention are suitably made of glass, but other organic or inorganic transparent materials may be employed.

"Unitary construction" and like terminology refers to structures consisting of a single shaped piece such as segmented rectangular structures as seen in the various Figures. Unitary construction includes composite structures such as laminated structures having bonded layers and structures having bonded segments and so forth. Monolithic structures are particularly preferred unitary structures in connection with the practice of the present invention as is discussed below.

Construction and operation of the device is described in connection with FIGS. 1-10C, appended hereto.

Figure 2:
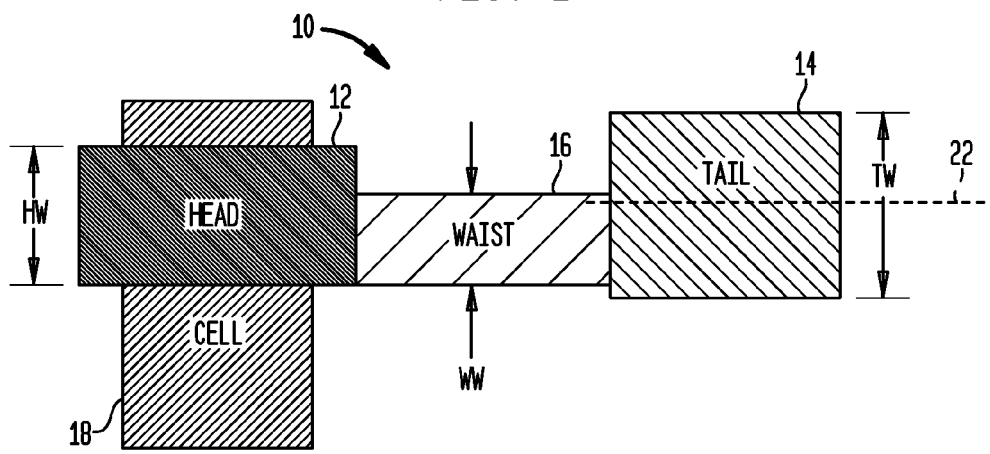
FIG. 2 is a schematic top view of a cell grabber of the invention bonded to a single cell.

Referring to FIGS. 1 and 2, there is shown schematically a cell grabber 10 having a monolithic structure which includes a "head" 12 having a length, HL, of 150 microns, a mounting portion including a "tail" 14 having a length, TL, of 3.35 mm, a "waist" 16 having a length, WL, of 1.5 mm such that the overall device has an overall length, L, of 5 mm. Head 12 has a concave bonding surface 20 which is coated with an adhesive and attaches to a cell 18, as shown in FIGS. 1 and 2. Tail 14 is connected to a force measuring system such as a MyoStretcher® system available from IonOptix by way of a carbon fiber (not shown) or the cell grabber can be connected to a force transducer in any of the systems described in the literature, as noted above, or may be connected to a static fixture or may be connected to a suitable motor for purposes of imposing stretches upon the cell.

Head 12, waist 16 and tail 14 have rectangular cross-sections, all of which have the same height, H, of about 100 microns, as shown in FIGS. 1 and 2; however, each portion may have a different width, as shown in FIG. 2. Thus, head 12 may have a width, HW, which is less than the tail width, TW, but greater than the waist width, WW. Adjusting the waist width "tunes" the stiffness of the overall grabber in cases where that is important. If a stiff grabber is desired, the waist will have the same width as the tail.

Tail 14 is typically the largest portion of the device and defines a central plane of lateral symmetry 22, as shown in FIG. 2, along the central axis of tail 14.

Note the lateral offset of the head (and optionally waist) with respect to plane 22. This geometry permits determining the top/bottom of the device by visual inspection since the device is asymmetric when viewed from the top or bottom. The head, waist and tail are preferably never the same width so that it is possible to create and observe this asymmetry for purposes of determining orientation. In cases where the waist is the same dimension as the tail and the head is smaller, the head may be offset from plane 22 in the direction indicated.

The grabber is preferably cut from a single piece of glass using laser micromachining or photolithography. A hybrid laser/photolithography technique is especially useful wherein one uses lasers to selectively pretreat the glass. The glass is then subsequently acid etched to remove the areas that were pretreated by the lasers, leaving the desired shape in the untreated glass. The hybrid technique is basically lithography where the laser treatment forms the mask (actually a mask negative), followed by acid treatment to remove material. The procedure is less damaging to the glass than traditional laser machining and results in a more robust product. That is, there are structural differences in the product depending upon the fabrication technique, regardless of geometry of the final product. Without intending to be bound by any theory, it is believed the laser alters the molecular structure of the exposed material, making it more soluble in acid which has minimal destructive effect on the remaining material after etching.

The height of the grabber depends on the thickness of the glass being used. Because it is difficult to remove material in this dimension, it is preferred to minimize profile changes in the side view, that is, along the height as shown in FIG. 1. This contrasts greatly with the top view where almost any profile can be cut with ease, that is the widths of the various sections are readily adjusted. The overall length of the grabber and the lengths of the individual sections may be fixed as shown in FIGS. 1 and 2 for manufacturing convenience.

Generally speaking, the shape and dimensions of the head determine the physical compatibility of the connection with the cell and also the strength of the bond to the cell. There are a number of different options for head shape and width as discussed in connection with various cell types. The waist width is often the same as that of the tail. However narrower widths are employed when it is desired to have a lower stiffness such as when allowing auxatonic contractions. The waist is always 1.5 mm long in one embodiment. Since one should never attach any part of the narrow width style waist to the carbon fiber member of a force measurement system such as the Myo Stretcher® force measurement system, this implies that the shortest length of grabber that will be protruding from the force transducer system is 1.650 mm if you have the narrow waist width style waist and the entire tail is joined to the force measurement system. For cases where tail and waist width are the same, a matched/tail/waist width or an "MT" style waist, this is not a consideration and the shortest distance protruding from the force measurement system is the head length, for example, 150 microns as shown in FIG. 1.

Grabber tail 14 is preferably rectangular in cross-section and its width is either the same as the head or the same as the height, whichever is larger. This assures that the mounting portion of the device is never taller than it is wide which prevents it from "falling over" when it is being waxed to or otherwise attached to its mount. The tail length is about 3.5 mm in most cases which is enough length to provide for attachment to a carbon fiber or other connecting member and also should permit easy handling of the grabber.

Figure 3:
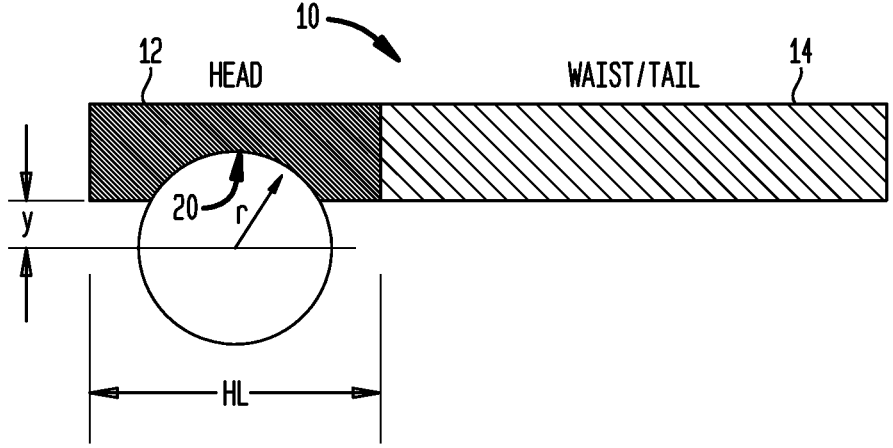
FIG. 3 is a schematic side view in elevation and section illustrating geometry of the inventive cell grabber head and support.
Figure 4:
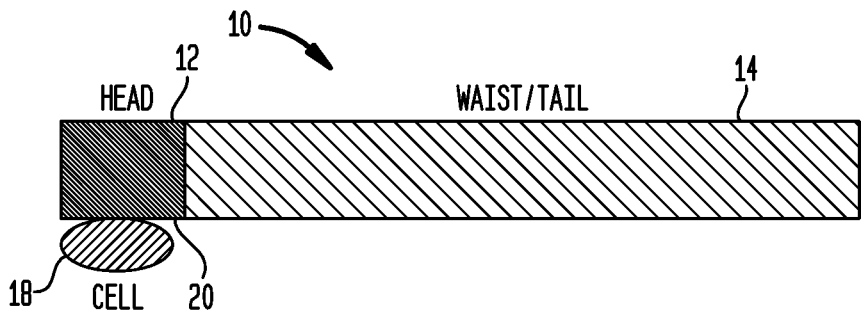
FIGS. 4-8 are schematic illustrations in elevation and section of a variety of cell grabber heads with different geometries bonded to single cells having different sizes and shapes.
Figure 5:
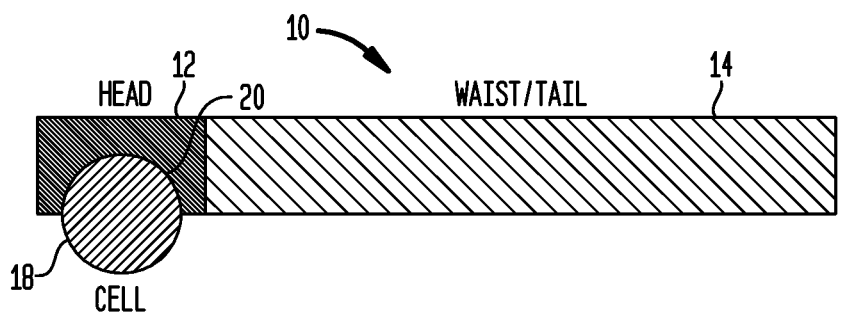
Figure 6:
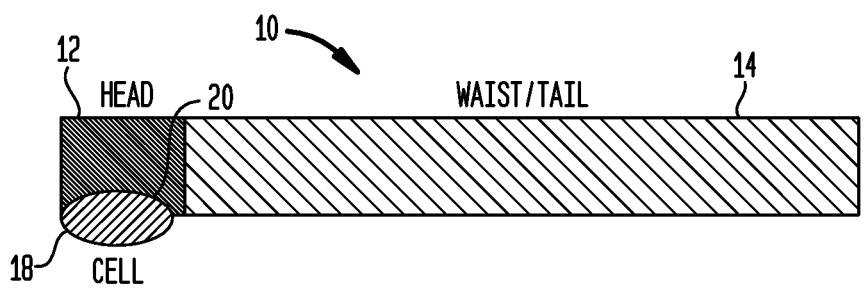
Figure 7:
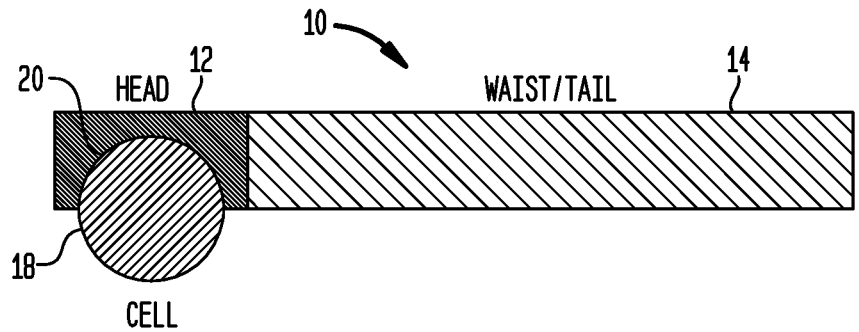
Figure 8:
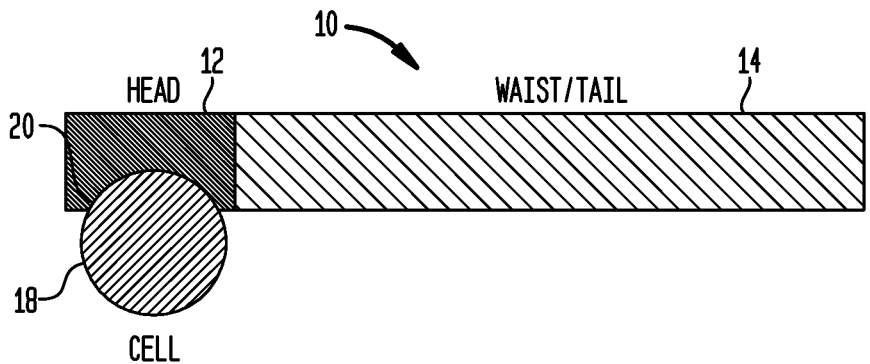

There are a variety of head shapes which are conveniently fabricated. These are based on a cylindrical section of material being removed from the raw material. A two-number system may be used to identify the head shape. The first number is the radius (r) of the circle and the second number is the offset of the center of the circle from the bottom of the material (y) as shown in FIG. 3. Thus a head shape identifier may be of the form r.y. For example, an r value of 50.0 would indicate a 100 um diameter semicircle being cut from the material. Note in FIG. 3 the head length (HL) is shown. This dimension may be fixed at 150 um so as to give no less than a cell width of space between the grabbing area and the waist for even the widest cells. Further options and adjustments may be made. The radii may be chosen based on the variety of cell envisioned and there are corrections to the geometry to accommodate the MyoTak® precoat and glue thicknesses. The MyoTak® precoat is assumed to be approximately 5 microns in total thickness and the glue film has a similar thickness. Since the cell presses into the glue quite a bit, the thickness of the aggregate pre-coat need not be accounted for in the nomenclature system. Therefore, the radius selected is typically 5 um larger than the nominal radius of the cell. Following are some examples.

HS0-0 is simply a flat surface. It is designed for cells such as cardiac myocytes that are oval in shape with a very thin vertical dimension as is shown schematically in FIG. 4.

HS30-0 is designed for 50 um nominal diameter circular cross section cells, primarily skeletal myocytes. It provides contact around the top half of the cell (180 degrees), as shown schematically in FIG. 5.

HS30-28 is designed for cells such as cardiac myocytes that are oval in shape with a very thin vertical dimension. It has a 2 um depression that is approximately 21 um in length, as shown schematically in FIG. 6.

HS35-0 is designed for 60 um nominal diameter circular cross section cells, primarily skeletal myocytes. It provides contact around the top half of the cell (180 degrees), as shown schematically in FIG. 7.

HS35-17 is designed for 60 um nominal diameter circular cross section cells, primarily skeletal myocytes. It provides contact around the top third of the cell (120 degrees), as shown schematically in FIG. 8.

A more detailed cell grabber part numbering and selection system may include four different codes separated by dashes as shown below:

HS-HW-WS-H

Sample geometries are tabulated below in Tables 1A, 1B and 1C. All dimensions are in microns.

TABLE 1A

| Grabber Head Selection | | | | | |
|---|---|---|---|---|---|
| HS-Head | | HW-Head Width | | | |
| Shape | Target Cell Type | 25 | 50 | 75 | 125 |
| HS0.0 | Cardiac | x | x | | |
| HS30.0 | Skeletal | | | x | x |
| HS30.28 | Cardiac | x | x | | |
| HS35.0 | Skeletal | | | x | x |
| HS35.17 | Skeletal | | | x | x |

TABLE 1B

| Grabber Style | |
|---|---|
| WS-Waist Style | |
| MT | Match Tail |
| KS2 | Known Stiffness (2N/m nominal) |

TABLE 1C

| Height Selection H-Overall Height |
|---|
| 75 |
| 100 |

EXAMPLES

HS30.0-75-MT-100 HS30.0 head shape 75 um wide, waist width matches tail, 100 um height.

Further Examples for grabber geometries are provided in Table 2.

TABLE 2

| Cell Grabber Geometries Tail/Waist Characteristics | | | | |
|---|---|---|---|---|
| Height | 75 | | 100 | |
| KS2 Waist Width (um) | 17.3 | | 15.7 | |
| Head Width | 25, 50, 75 | 125 | 25, 50, 75 | 125 |
| Tail Width ( also MT Waist Width) | 75 | 150 | 100 | 150 |

Figure 9:
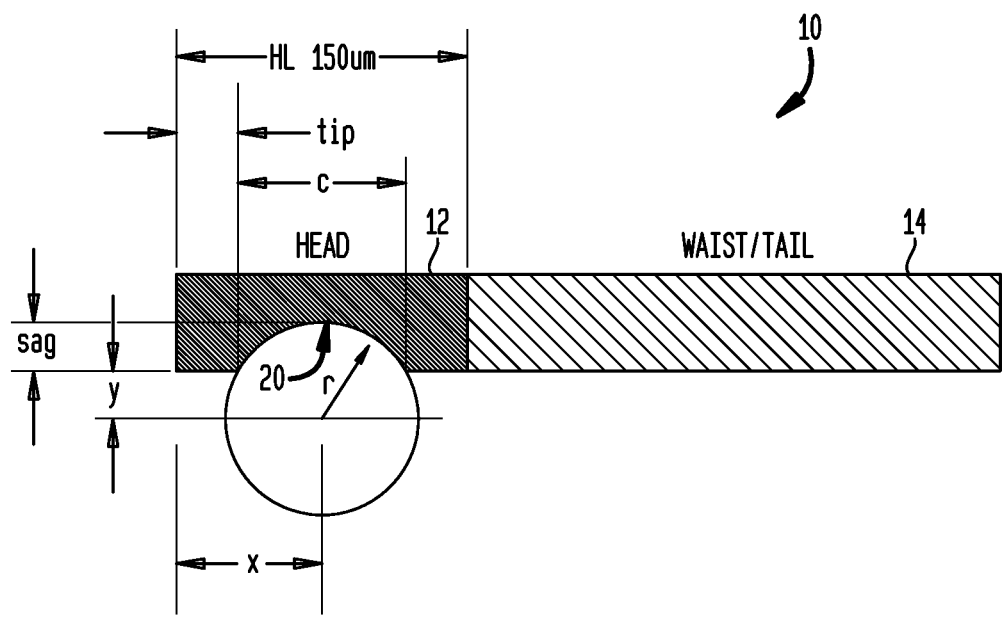
FIG. 9 is a schematic view in elevation and section of a cell grabber of the invention illustrating details of construction of the device.

Additional features on construction are appreciated by reference to FIG. 9 which is a view in elevation and section of a cell grabber wherein y indicates the distance from the grabber head of the radius of curvature, r, of the cylindrical section bonding surface 20 of the grabber head.

TABLE 3

| HS—Head Shape | r | y | tip* | sag—Sagitta | c—Chord | x (tip + c/2) |
|---|---|---|---|---|---|---|
| HS0.0 | 0 | 0 | 5 | 0 | — | — |
| HS30.0 | 30 | 0 | 5 | 30 | 60 | 35 |
| HS30.28 | 30 | 28 | 5 | 2 | 21.5 | 15.8 |
| HS35.0 | 35 | 0 | 5 | 35 | 70 | 40 |
| HS35.17 | 35 | 17 | 5 | 18 | 61.2 | 35.6 |

*The tip dimension is to be the minimum distance that can be manufactured reasonably. Here it is assumed to be 5 um.

The cell grabbers of the invention are conveniently fabricated from a single piece substrate such as a 100 micron thick glass cover slip or other suitable material by machining or etching the slip with a laser or other suitable technology such as photolighography. In this way, a single sheet of material is used to make a multiplicity of cell grabbers, for example, 20 or more in a comb-like structure by laser etching. The cell grabbers remain attached to an un-etched portion or residual member of the substrate as illustrated in FIGS. 10-10C.

Figure 10:
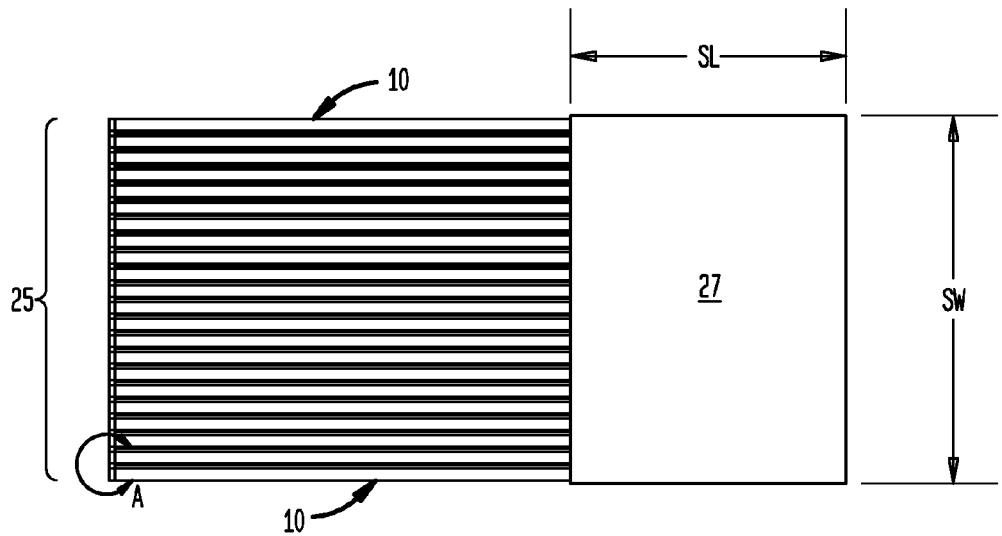
FIGS. 10, 10A, 10B and 10C illustrate an ensemble of cell grabbers of the invention laser-etched from a glass substrate.

FIG. 10 is a plan view of an ensemble of cell grabbers 25 attached to a residual member 27 of glass sheet from which grabbers 10 can be detached.

Figure 10A:
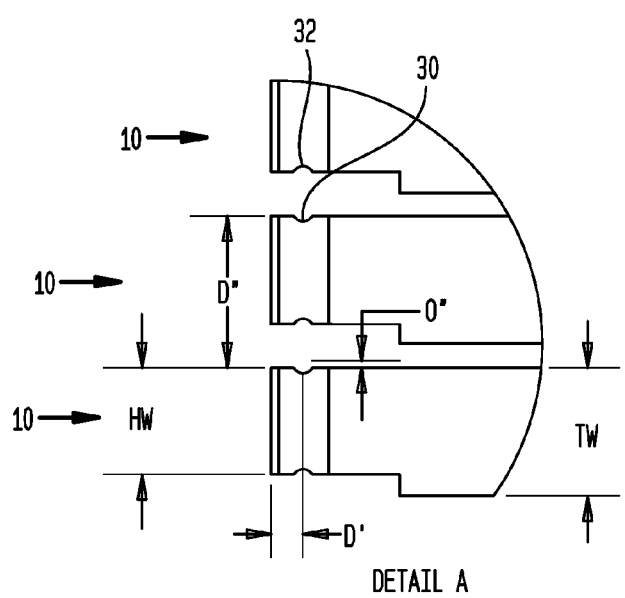
Figure 10B:
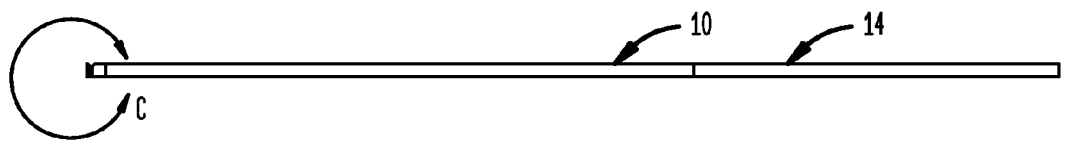
Figure 10C:
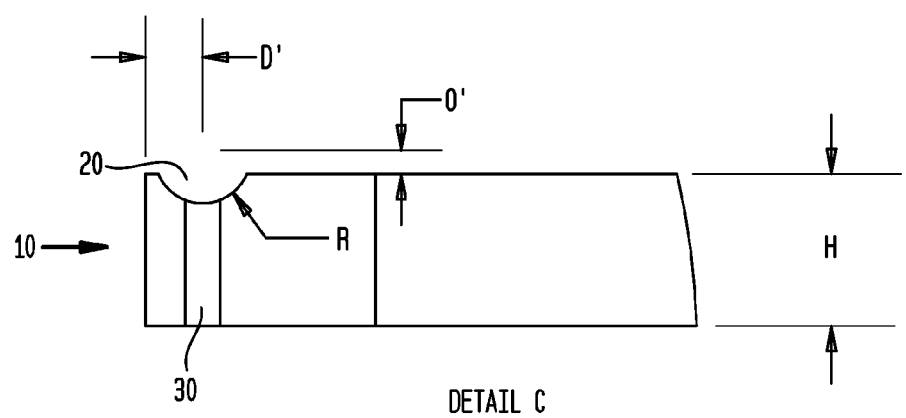

FIG. 10A is a detail (scale 100:1) showing a top view of a plurality of cell grabbers 10 of ensemble 25, especially illustrating head geometry. FIG. 10B is a side view of a grabber 10, and FIG. 10C is an enlarged detail of FIG. 10B, further illustrating the cell grabber head geometry.

Residual member 27 has a substrate width, SW, of about 4 mm and a substrate length, SL, of about 3 mm. Attached to member 27 are more than 20 cell grabbers 10 of ensemble 25 having the geometries seen in FIGS. 10A, 10B and 10C.

FIG. 10C is a side view in elevation of cell grabber 10 wherein the cylindrical bonding surface 20 is oriented upwardly and has a radius of curvature, R, of 35 microns. The origin of R is offset from the surface of the grabber head a distance 0' of 17 microns such that the depth of bonding surface 20 is likewise about 17 microns and the cylindrical profile of the concave bonding surface extends over less than 180°. The center of section 20 is a distance, D', of about 36 microns from the tip of the grabber head and the grabber has a height of about 10 microns. The waist and tail are attached and have a width, TW, of 150 microns, while the grabber head has a width, HW, of 125 microns. The grabbers of ensemble 25 repeat every repeat distance, D", of 180 microns.

For purposes of providing a visual marker for the center of the bonding surface 20, there are provided a pair of perpendicular grooves 30, 32 on each grabber. These grooves may likewise have a cylindrical section profile with a radius of curvature, having an origin offset form the side of the grabber head a distance, O", of 10 microns or so (FIG. 10A) when the radius of curvature of the groove is 15 microns such that the grooves have a depth of 5 microns. Of course, other dimensions are possible for the various embodiments of the cell grabber which can be tailored to accommodate different types of cells and tissue as discussed above.

Figure 11B:
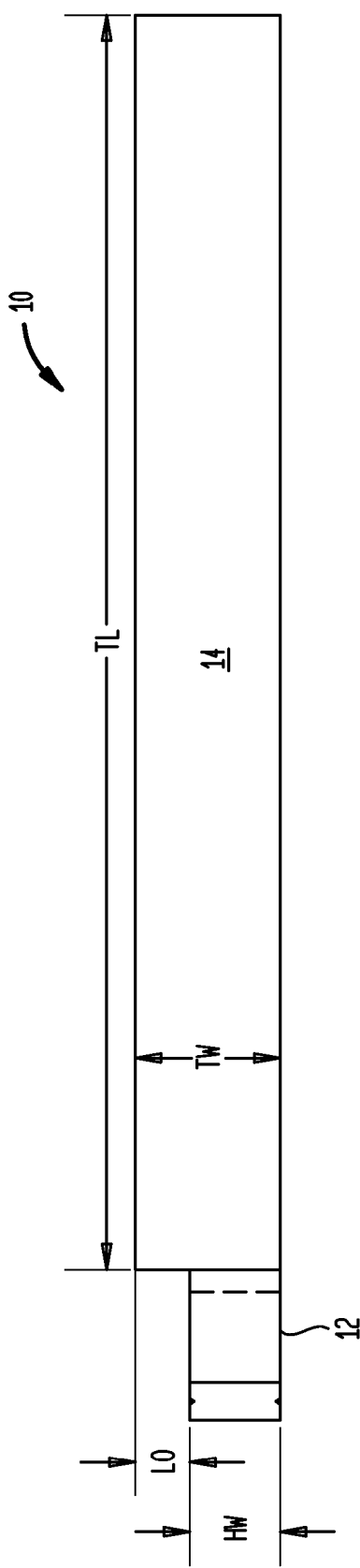
FIG. 11B is a top view of the cell grabber of FIG. 11A.
Figure 11C:
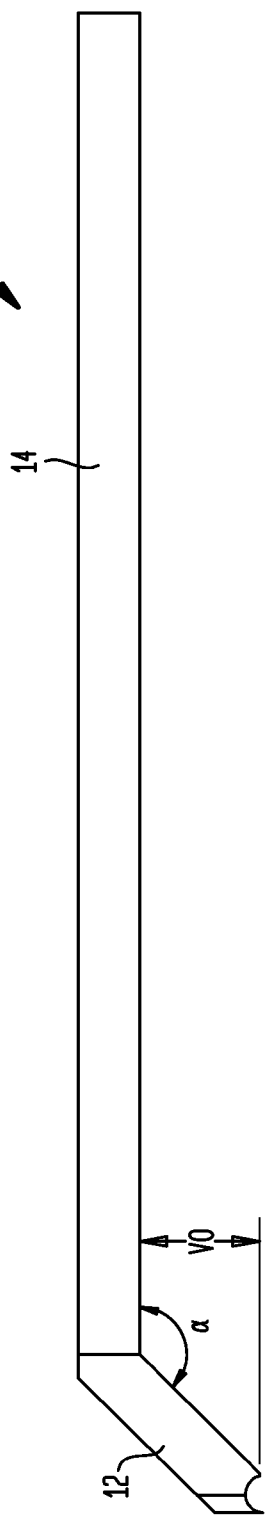
FIG. 11C is a side view of the cell grabber of FIG. 11A.
Figure 12A:
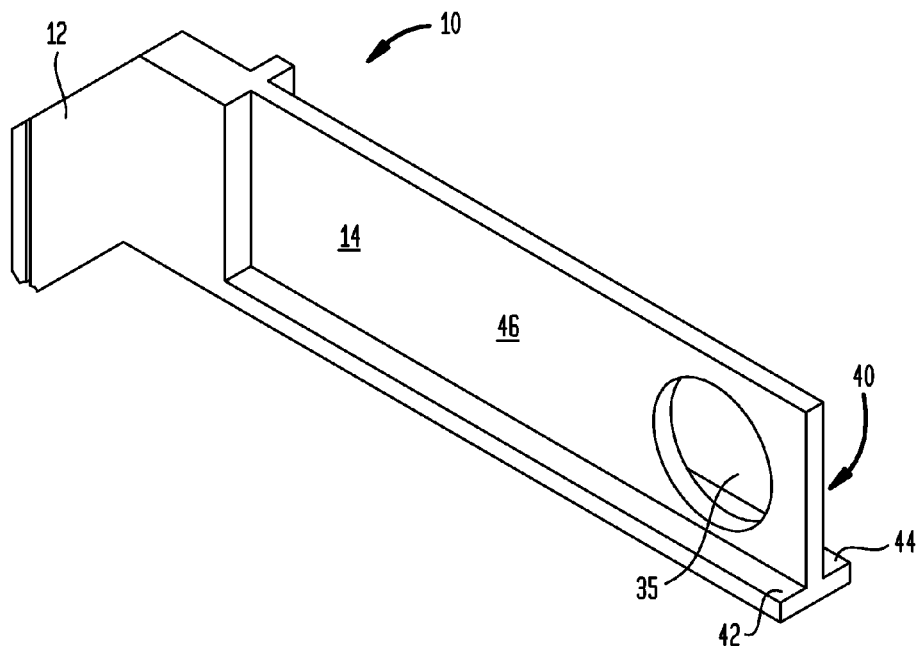
FIG. 12A is a view in perspective of yet another embodiment of a cell grabber of the present invention.
Figure 12B:
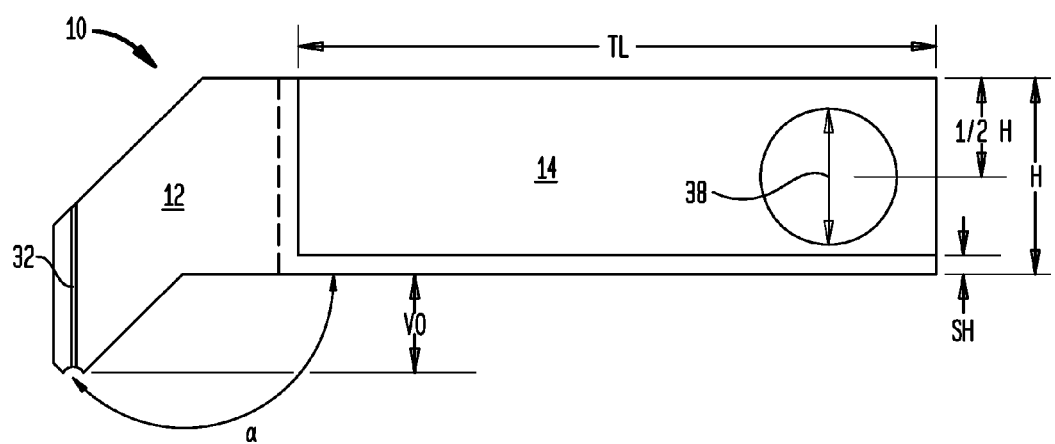
FIG. 12B is a side view of the cell grabber of FIG. 12A.
Figure 12C:
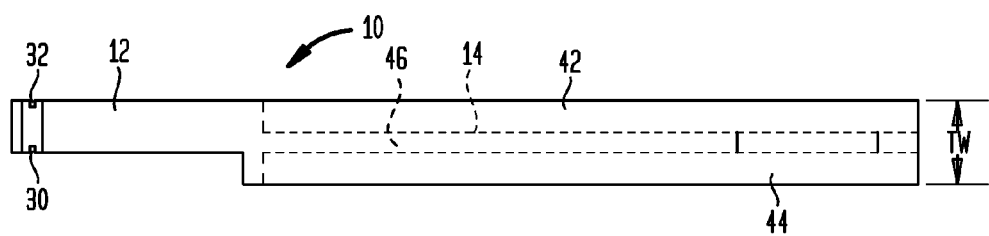
FIGS. 12C and 12D are schematic bottom and top views respectively of the cell grabber of FIG. 12A.
Figure 12D:
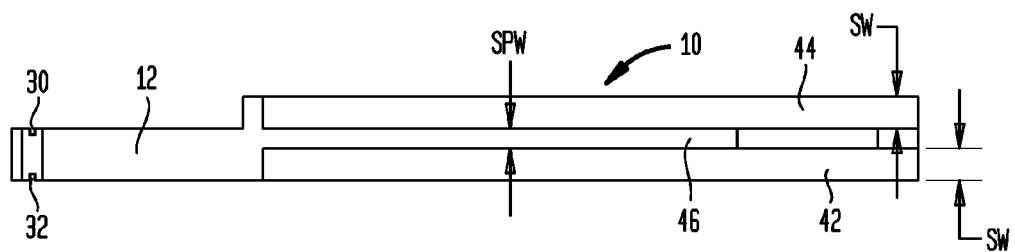

Referring to FIGS. 11A-11C, there is shown another embodiment of a cell grabber 10 in accordance with the invention having the various features described above, except that head 12 is laterally and vertically offset from the tail 14, as shown. Generally, the lower edge of head 12 is vertically offset from the lower side of the tail a vertical offset height, VO, of anywhere from about 100 to 1000 microns, greater than 100 microns being preferred, while the head is laterally offset form the tail's distal outer edge a lateral distance, LO, of about 100 microns or so. LO may be anywhere from 25 microns to 150 microns for a cell grabber having a tail width, TW, of 300 microns or so.

Note that head 12 defines an included angle, α, with tail 14. α may be anywhere from about 90° to 160°, typically about 135°.

The embodiment of FIGS. 11A-11C is substantially the same as those shown in FIGS. 1-10C that except the head is offset from the axis of the waist/tail to make alignment easier so that the tip always hits the bottom of the sample chamber first with this design which is not necessarily the case with the straight design.

FIGS. 12A-12D show yet another embodiment of the present invention similar to that of FIGS. 11A-11C. This design removes almost all the waist/tail material while retaining the head offset. The main design goal is to minimize weight. Grabber 10 as shown in FIGS. 12A-12D includes a tail portion 14 with a circular hole 35 which reduces weight and is useful for manipulating the device, for example, to receive a glass fiber and position the cell gabber for adhesive coupling to another component of a measurement system. Hole 35 may have a diameter 38 of 150 microns or so for a tail having a height H of 200 microns. A T shaped end profile 40 defined by the tail further reduces weight and can eliminate most of the material in the tail. The configuration includes a pair of lower shelves 42, 44 and a central spline 46. Each of shelves 42, 44 a shelf width SW and spline 46 has a spline width SPW. For a grabber 10 having a tail width TW of 80 microns of so, SW values of 30 microns or so are suitable. In other words, 2×SW is greater than SPW such that more than half of the weight of the tail may be removed by a hybrid laser/photolithography technique, for example. The height of spline 46 is the same as tail height H, while shelves 42, 44 may have a shelve height, SH, of from 10-20 microns or so for a tail having a height of 100 microns. Typically SH is less than 25% of H, suitably 5% to 20% of H.

There is thus provided in accordance with the invention a cell grabber having a unitary structure including a transparent grabber head at a terminus thereof and an elongated mounting portion extending therefrom, the grabber head being configured and adapted to bond to a live tissue specimen and having a bonding surface which is either planar or concave. The bonding surface may be concave and define a cylindrical section profile with a radius of curvature of from about 10 microns to about 100 microns, more preferably the cylindrical section profile of the bonding surface has a radius of curvature of from about 20 microns to about 50 microns. Typically, the radius of curvature of the bonding surface has an origin that is offset from the unitary structure such that the cylindrical profile of the bonding surface has an angular extent of less than 180 degrees and a depth of less than its radius of curvature.

In one preferred embodiment, the transparent grabber head has a pair of lateral grooves extending perpendicularly with respect to the concave bonding surface and being located centrally with respect to the concave grabber surface in order to provide a visual marker for the central area of the concave bonding surface. The lateral grooves may define cylindrical profiles with radii of curvature offset from the from the monolithic rectangular structure such that the cylindrical profiles of the grooves have angular extents of less than 180 degrees and depths of less than their radius of curvature such that the lateral grooves have a depth of from about 1 to about 10 microns. More preferably, the lateral grooves have a depth of from about 2.5 microns to about 7.5 microns.

A particularly preferred configuration is wherein the unitary structure is rectangular. The width of the unitary rectangular structure mounting portion may be greater than its height and the bonding surface is disposed on an upper or lower surface of the grabber head. In some embodiments, the width of the grabber head is less than that of the mounting portion of the monolithic structure, the mounting portion of the monolithic structure defines a central plane of lateral symmetry and the grabber head is laterally offset with respect to the central plane of lateral symmetry of the mounting portion of the monolithic structure such that the lateral position of the grabber head with respect to the central plane of lateral symmetry of the mounting portion of monolithic structure is indicative of the orientation of the monolithic structure.

The cell grabber may further comprise a waist portion intermediate the grabber head and mounting portion having a width smaller than the mounting portion, especially wherein the mounting portion of the unitary structure defines a central plane of lateral symmetry and the waist portion is laterally offset with respect to the central plane of lateral symmetry of the mounting portion of the unitary structure such that the lateral position of the waist portion with respect to the central plane of lateral symmetry of the unitary structure is indicative of the orientation of the unitary structure. In such cases the waist portion of the cell grabber may be dimensioned with a width of from about 25% to 85% of the width of the mounting portion so as to provide a pre-determined stiffness to the cell grabber.

Generally, the cell grabber has a length of from about 1 to about 25 mm, the mounting portion has a height of from about 25 to 400 microns and the mounting portion has a width of from about 50 to about 500 microns. Typical dimensions are wherein the cell grabber has a length of from about 2.5 mm to about 10 mm, the mounting portion has a height of from about 50 microns to about 200 microns and the mounting portion has a width of from about 50 microns to about 300 microns. Typical dimensions are wherein the cell grabber head has a length of from about 50 to about 450 microns, a width of from about 30 to about 300 microns and a height of from about 25 to 400 microns. Preferred dimensions include wherein the cell grabber head has a length of from about 150 to about 300 microns, a width of from about 75 to about 300 microns and a height of from about 50 microns to about 200 microns.

In any embodiment, the unitary structure is a monolithic structure which may be fabricated from glass by way of laser machining a planar blank and wherein the mounting portion of the cell grabber is likewise transparent.

In any embodiment, the cell grabber may be fabricated from glass by way of photolithography from a planar blank and wherein the mounting portion of the cell grabber is likewise transparent.

In any embodiment, the bonding surface of the cell grabber head may be coated with an adhesive. The adhesive may be a biocompatible adhesive comprising an extracellular matrix including a component selected from collagens, non-collagenous glycoproteins, and proteoglycans. The adhesive may comprise an extracellular matrix including a component selected from laminin, collagen type I, collagen type II, collagen type III, collagen type IV, collagen type V, elastin, entactin, fibronectin, tenascin, heparin sulfate, chondroitan sulfate, dermaten sulfate, or karatan sulfate. The adhesive may be a biocompatible adhesive comprising an extracellular matrix gel or a biocompatible adhesive comprising a matrix protein derived from Engelbreth Holm-Swarm sarcoma. The adhesive may include a bond strength agent selected from collagen type IV, laminin, and chitosan.

In any embodiment, the adhesive may be coated onto the bonding surface as a film having a thickness of from about 2 microns to about 10 microns, such as of from about 3 microns to about 7 microns.

In a preferred embodiment, the adhesive is a biocompatible adhesive comprising an aggregate selected from include alumina silicate or diamond powder and/or the adhesive is a biocompatible adhesive comprising bovine serum albumin conjugated with a fluorophore.

In one application of the invention, there is provided an ensemble of cell grabbers etched from a planar substrate comprising a plurality of cell grabbers having a monolithic structure including a transparent grabber head at a terminus thereof and an elongated mounting portion extending therefrom, the grabber head being configured and adapted to bond to a live tissue specimen and having a bonding surface which is either planar or concave, the mounting portions of each cell grabber having a terminus distal to said grabber head and being affixed to a residual carrier member of the planar substrate from which the ensemble was etched which is thereby integral with the cell grabbers. The substrate may be a glass substrate and/or said substrate is laser etched or is etched by way of photolithography. The ensemble may include from about 10 to about 100 cell grabbers.

In another application of the invention, there is provided a method of measuring tensile characteristics of a live tissue specimen comprising:
(a) attaching the tissue specimen to a bonding surface of a cell grabber with a suitable adhesive, the cell grabber having a unitary structure including a transparent grabber head at a terminus thereof and an elongated mounting portion extending therefrom, the grabber head having the bonding surface which is either planar or concave and coated with the adhesive in order to secure the cell;
(b) connecting the cell grabber to a force transducer; and
(c) measuring the force applied by the tissue specimen.

The live tissue specimen may be a single cell such as a myocyte selected from skeletal myocytes and cardiac myocytes.

The method is suitably practiced wherein the single cell is attached to 2 cell grabbers, each of which has a unitary structure including a transparent grabber head at a terminus thereof and an elongated mounting portion extending therefrom, the grabber heads having the bonding surface which is either planar or concave and coated with the adhesive in order to secure the cell. The measurement may be taken wherein the force applied by the cell is measured auxotonically, isotonically or isometrically.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the Summary of Invention and Detailed Description, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A cell grabber having a unitary structure including a transparent grabber head at a terminus thereof and an elongated mounting portion extending therefrom, the grabber head being configured and adapted to bond to a live tissue specimen and having a bonding surface which is concave, wherein the concave surface defines a cavity with a surface area larger than its projected perpendicular area; and
wherein the grabber head has a width of up to 300 microns and a length of up to 450 microns and wherein further the concave bonding surface defines a cylindrical section profile with a radius of curvature.

2. The cell grabber according to claim 1, wherein the cylindrical section profile of the bonding surface has a radius of curvature of from about 10 microns to about 100 microns.

3. The cell grabber according to claim 1, wherein the radius of curvature of the bonding surface has an origin that is offset from the unitary structure such that the cylindrical profile of the bonding surface has an angular extent of less than 180 degrees and a depth of less than its radius of curvature.

4. The cell grabber according to claim 1, wherein the cell grabber is etched from a glass substrate using a hybrid laser/photolithography technique so as to provide a monolithic structure.

5. The cell grabber according to claim 1, wherein the unitary structure has a rectangular grabber head and a rectangular mounting portion.

6. The cell grabber according to claim 5, wherein the width of the unitary rectangular mounting portion is greater than its height and the bonding surface is disposed on an upper or lower surface of the grabber head.

7. The cell grabber according to claim 5, wherein the width of the grabber head is less than that of the mounting portion of the unitary structure, the mounting portion of the unitary structure defines a central plane of lateral symmetry and the grabber head is laterally offset with respect to the central plane of lateral symmetry of the mounting portion of the unitary structure such that the lateral position of the grabber head with respect to the central plane of lateral symmetry of the mounting portion of the unitary structure is indicative of the orientation of the monolithic unitary structure.

8. The cell grabber according to claim 1, wherein the grabber head is vertically offset with respect to the mounting portion.

9. The cell grabber according to claim 1, wherein the bonding surface of the cell grabber head is coated with an adhesive.

10. A cell grabber having a unitary structure including a transparent grabber head at a terminus thereof and an elongated mounting portion extending therefrom, the grabber head being configured and adapted to bond to a live tissue specimen and having a bonding surface which is either planar or concave, wherein:
when the bonding surface is planar, the planar surface is substantially flat on a cellular scale, optionally having convexity or concavity with a radius of curvature more than 1 mm;
or when the bonding surface is concave, the concave surface defines a cavity with a surface area larger than its projected perpendicular area; and
wherein further the grabber head has a width of up to 300 microns and a length of up to 450 microns and wherein the unitary structure has a rectangular grabber head and a rectangular mounting portion wherein the cell grabber further comprises a waist portion intermediate the grabber head and mounting portion having a width smaller than the mounting portion.

11. The cell grabber according to claim 10, wherein the mounting portion of the unitary structure defines a central plane of lateral symmetry and the waist portion is laterally offset with respect to the central plane of lateral symmetry of the mounting portion of the unitary structure such that the lateral position of the waist portion with respect to the central plane of lateral symmetry of the unitary structure is indicative of the orientation of the unitary structure.

12. The cell grabber according to claim 11, wherein the waist portion of the cell grabber is dimensioned with a width of from about 25% to 85% of the width of the mounting portion so as to provide a pre-determined stiffness to the cell grabber.

13. The cell grabber according to claim 5, wherein the rectangular mounting portion has a T-shaped end profile.

14. An ensemble of cell grabbers etched from a planar substrate comprising a plurality of cell grabbers having a monolithic structure including a transparent grabber head at a terminus thereof and an elongated mounting portion extending therefrom, the grabber head being configured and adapted to bond to a live tissue specimen and having a bonding surface, the mounting portions of each cell grabber having a terminus distal to said grabber head and being affixed to a residual carrier member of the planar substrate from which the ensemble was etched which is thereby integral with the cell grabbers, wherein:
the bonding surface is concave and the concave surface defines a cylindrical section profile with a radius of curvature; and
wherein further the grabber head has a width of up to 300 microns and a length of up to 450 microns.

15. The ensemble according to claim 14, wherein said substrate is a glass substrate.

16. A cell grabber having a unitary structure including a transparent grabber head at a terminus thereof and an elongated mounting portion extending therefrom, the grabber head being configured and adapted to bond to a live tissue specimen and having a bonding surface wherein:
the bonding surface is concave and the concave surface defines a cylindrical section profile with a radius of curvature; and
wherein further the grabber head has a width of up to 300 microns and a length of up to 450 microns;
wherein the unitary structure has a rectangular grabber head and a rectangular mounting portion and the width of the grabber head is less than that of the mounting portion of the unitary structure, the mounting portion of the unitary structure defines a central plane of lateral symmetry and the grabber head is laterally offset with respect to the central plane of lateral symmetry of the mounting portion of the unitary structure such that the lateral position of the grabber head with respect to the central plane of lateral symmetry of the mounting portion of monolithic structure is indicative of the orientation of the monolithic structure and wherein the grabber head is vertically offset with respect to the mounting portion.

17. A cell grabber having a unitary structure including a transparent grabber head at a terminus thereof and an elongated mounting portion extending therefrom, the grabber head being configured and adapted to bond to a live tissue specimen and having a bonding surface which is concave, wherein the transparent grabber head has a pair of lateral grooves extending perpendicularly with respect to the concave bonding surface and being located centrally with respect to the concave grabber surface in order to provide a visual marker for the central area of the concave bonding surface, wherein the concave surface defines a cylindrical section profile with a radius of curvature and wherein further the grabber head has a width of up to 300 microns and a length of up to 450 microns.

18. A method of measuring tensile characteristics of a live tissue specimen comprising:
(a) attaching the tissue specimen to a bonding surface of a cell grabber with a suitable adhesive, the cell grabber having a unitary structure including a transparent grabber head at a terminus thereof and an elongated mounting portion extending therefrom, the grabber head having the bonding surface coated with the adhesive in order to secure the cell, wherein:
the bonding surface is concave and the concave surface defines a cylindrical section profile with a radius of curvature; and
wherein further the grabber head has a width of up to 300 microns and a length of up to 450 microns;
(b) connecting the cell grabber to a force transducer; and
(c) measuring the force applied by the tissue specimen.

19. The method of measuring tensile characteristics of a sue specimen according to claim 18, wherein the live tissue specimen is a single cell.

20. The method of measuring tensile characteristics of a sue specimen according to claim 18, wherein the single cell is attached to 2 cell grabbers, each of which has a unitary structure including a transparent grabber head at a terminus thereof and an elongated mounting portion extending therefrom, the grabber heads having the bonding surface coated with the adhesive in order to secure the cell.

* * * * *